(12) United States Patent
Glenn, Jr. et al.

(10) Patent No.: US 8,550,095 B2
(45) Date of Patent: Oct. 8, 2013

(54) SYSTEM FOR HIGHLIGHTING HAIR

(75) Inventors: Robert Wayne Glenn, Jr., Liberty Township, OH (US); Simon Paul Godfrey, Uxbridge (GB); Gemma Zoe Smithers, Cheam (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/363,459

(22) Filed: Feb. 1, 2012

(65) Prior Publication Data

US 2012/0152271 A1 Jun. 21, 2012

Related U.S. Application Data

(62) Division of application No. 12/135,280, filed on Jun. 9, 2008, now Pat. No. 8,132,570.

(30) Foreign Application Priority Data

Jun. 15, 2007 (EP) .................................... 07110394

(51) Int. Cl.
*A45D 19/18* (2006.01)
*A61K 8/18* (2006.01)

(52) U.S. Cl.
USPC .......................................... 132/270; 132/208

(58) Field of Classification Search
USPC ........................................ 132/208, 108, 270
See application file for complete search history.

(56) References Cited

U.S. PATENT DOCUMENTS

| | | |
|---|---|---|
| 2,272,409 A | 2/1942 | Johnson |
| 2,310,295 A | 2/1943 | Keele |
| 2,776,667 A | 1/1957 | Fitzgerald |
| 3,030,968 A | 2/1960 | Oberstar |
| 2,962,031 A | 11/1960 | Bumgarner |
| 3,662,767 A | 5/1972 | Murtha |
| 3,702,508 A | 11/1972 | Netter |
| 3,921,647 A | 11/1975 | Fisher |
| 4,020,854 A | 5/1977 | Caruso |
| 4,108,184 A | 8/1978 | Morganroth |
| 4,398,549 A | 8/1983 | Thomas |
| 4,503,870 A | 3/1985 | Peterson |
| 4,796,812 A | 1/1989 | Grollier |
| 4,942,893 A | 7/1990 | Trottier |
| 5,042,514 A | 8/1991 | Bastien |

(Continued)

FOREIGN PATENT DOCUMENTS

| | | |
|---|---|---|
| DE | 662702 C1 | 7/1938 |
| DE | 197639177 U1 | 4/1977 |

(Continued)

*Primary Examiner* — Rachel Steitz
(74) *Attorney, Agent, or Firm* — James T. Fondriest

(57) ABSTRACT

A system to highlight the hair includes a device (10) and a composition (50). The device (10) includes a first portion movably joined to a second portion. Composition (50) includes a percentage of hydrogen peroxide and a percentage of an alkalizer by weight of the composition (50). The weight percentages of hydrogen peroxide and of an alkalizer are defined by equation (I): $X+1.5Y \geq 15$ (I). X is the percentage by weight of hydrogen peroxide by weight of the composition (50). Y is the percentage by weight of an alkalizer by weight of the composition (50). The composition (50) includes at least 2% of hydrogen peroxide by weight of the composition (50) and the alkalizer is an inorganic salt. The composition (50) allows to perform highlighting when applied with the device (10).

12 Claims, 4 Drawing Sheets

(56) References Cited

U.S. PATENT DOCUMENTS

| | | |
|---|---|---|
| 5,060,679 A | 10/1991 | Christopher et al. |
| 5,279,313 A | 1/1994 | Clausen |
| 5,535,764 A | 7/1996 | Abramson |
| 5,554,197 A | 9/1996 | Assini |
| 5,771,906 A | 6/1998 | De Benedictis |
| 5,823,204 A | 10/1998 | Todd |
| 5,848,730 A | 12/1998 | Kawase |
| 5,971,645 A | 10/1999 | Fukushima |
| 6,062,231 A | 5/2000 | De LaForcade |
| 6,148,829 A | 11/2000 | De Benedictis |
| 6,250,312 B1 | 6/2001 | Dasilva |
| 6,427,701 B1 | 8/2002 | Roth |
| 6,440,175 B1 | 8/2002 | Stanley |
| 6,626,599 B2 | 9/2003 | Delaforcade |
| 6,748,957 B1 | 6/2004 | Giordano |
| 7,025,069 B2 | 4/2006 | Thiebaut |
| 7,198,049 B2 | 4/2007 | Elmer |
| 7,357,137 B2 | 4/2008 | Husband |
| 7,425,220 B2 | 9/2008 | Barrass |
| 7,475,688 B2 | 1/2009 | Colacioppo |
| 7,543,591 B1 | 6/2009 | Munsil |
| 2002/0114657 A1 | 8/2002 | Gueret |
| 2002/0142027 A1 | 10/2002 | Gueret |
| 2003/0007825 A1 | 1/2003 | De LaForcade |
| 2003/0024544 A1 | 2/2003 | Thiebaut |
| 2004/0016064 A1 | 1/2004 | Vena |
| 2004/0031502 A1 | 2/2004 | Winckels |
| 2004/0089316 A1 | 5/2004 | Hamilton |
| 2004/0141931 A1* | 7/2004 | Narasimhan et al. ........... 424/62 |
| 2004/0182408 A1 | 9/2004 | De LaForcade |
| 2005/0079192 A1 | 4/2005 | Simon |
| 2005/0207153 A1 | 9/2005 | Leleve |
| 2005/0211599 A1 | 9/2005 | De LaMettrie |
| 2006/0042643 A1 | 3/2006 | Delan |
| 2006/0064824 A1 | 3/2006 | Godfrey |
| 2006/0090771 A1 | 5/2006 | Ramet |
| 2006/0144415 A1 | 7/2006 | Magee |
| 2006/0207036 A1 | 9/2006 | Kennedy |
| 2007/0144550 A1 | 6/2007 | Roher |
| 2007/0215170 A1 | 9/2007 | Kennedy |
| 2007/0227620 A1 | 10/2007 | Kunii |
| 2008/0000492 A1 | 1/2008 | Mills |
| 2008/0083418 A1 | 4/2008 | Glenn |
| 2008/0083419 A1 | 4/2008 | Glenn |
| 2008/0083420 A1 | 4/2008 | Glenn |
| 2008/0087292 A1 | 4/2008 | Abergel |
| 2008/0087293 A1 | 4/2008 | Glenn |
| 2008/0087294 A1 | 4/2008 | Glenn |
| 2008/0110929 A1 | 5/2008 | Stanley Traasdahl et al. |
| 2008/0156817 A1 | 7/2008 | Roseblade |
| 2008/0196734 A1 | 8/2008 | Husband |
| 2008/0223386 A1 | 9/2008 | Albisetti |
| 2008/0223391 A1 | 9/2008 | Baker |
| 2008/0223393 A1 | 9/2008 | Boyle |
| 2008/0257370 A1 | 10/2008 | Perry |
| 2008/0308119 A1 | 12/2008 | Smith |
| 2009/0050171 A1 | 2/2009 | Barrass |
| 2009/0071496 A1 | 3/2009 | Glenn |
| 2009/0084393 A1 | 4/2009 | Baker |
| 2009/0084394 A1 | 4/2009 | Baker |
| 2009/0084395 A1 | 4/2009 | Glenn |
| 2009/0095314 A1 | 4/2009 | Lund |
| 2009/0101159 A1 | 4/2009 | Bonnafous |
| 2009/0152281 A1 | 6/2009 | Bowes |
| 2009/0223531 A1 | 9/2009 | Lund |

FOREIGN PATENT DOCUMENTS

| | | |
|---|---|---|
| DE | 198805283 U1 | 7/1988 |
| DE | 3138389 C2 | 7/1990 |
| DE | 4041742 A1 | 6/1992 |
| DE | 29616331 U1 | 12/1996 |
| DE | 29917054 U1 | 8/2000 |
| DE | 10259016 A1 | 6/2004 |
| DE | 202004017014 U1 | 6/2005 |
| DE | 20221665 U1 | 11/2006 |
| DE | 102005058188 A1 | 6/2007 |
| DE | 202007016018 U1 | 4/2008 |
| EP | 1138374 A1 | 10/2001 |
| EP | 1566114 A1 | 8/2005 |
| EP | 1264559 B1 | 11/2005 |
| EP | 1897459 A1 | 3/2008 |
| EP | 1915920 A1 | 4/2008 |
| EP | 1481605 B1 | 8/2009 |
| FR | 2444421 A1 | 7/1980 |
| FR | 2495905 A1 | 6/1982 |
| FR | 2854778 A1 | 11/2004 |
| FR | 2905833 A1 | 3/2008 |
| GB | 274875 A | 10/1927 |
| GB | 2242357 A | 10/1991 |
| GB | 2383944 A | 7/2003 |
| GB | 2384425 A | 7/2003 |
| JP | 4-41305 | 4/1992 |
| JP | 11-178630 | 7/1999 |
| JP | 11-178639 A | 7/1999 |
| JP | 2001-211925 A | 8/2001 |
| JP | 2002-034636 A | 2/2002 |
| JP | 2003-199623 A | 7/2003 |
| JP | 2003-310337 A | 11/2003 |
| WO | WO 93/02589 A1 | 2/1993 |
| WO | WO 93/10687 A1 | 6/1993 |
| WO | WO 98/43511 A1 | 10/1998 |
| WO | WO 02/074129 A1 | 9/2002 |
| WO | WO 2006/010354 A1 | 2/2006 |

* cited by examiner

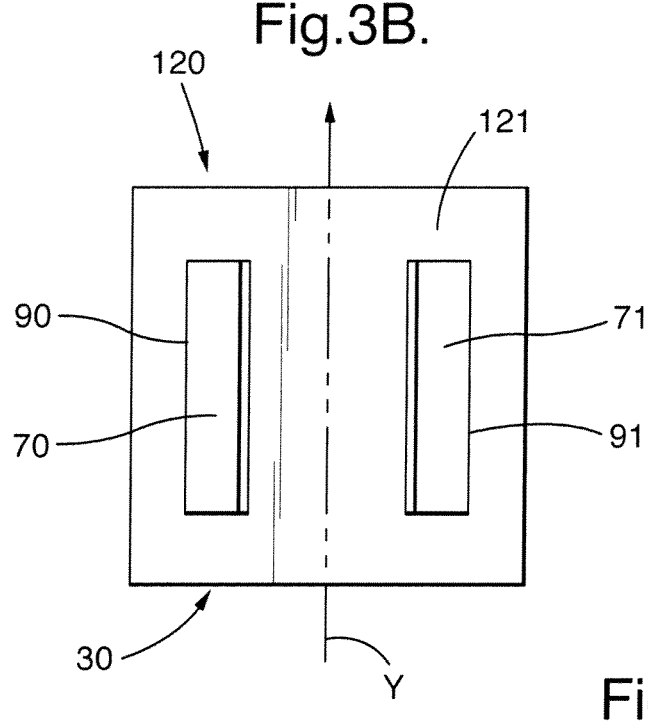
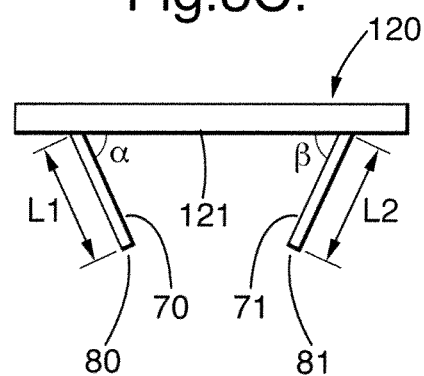
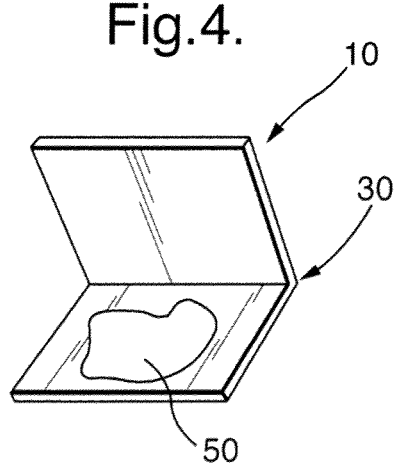

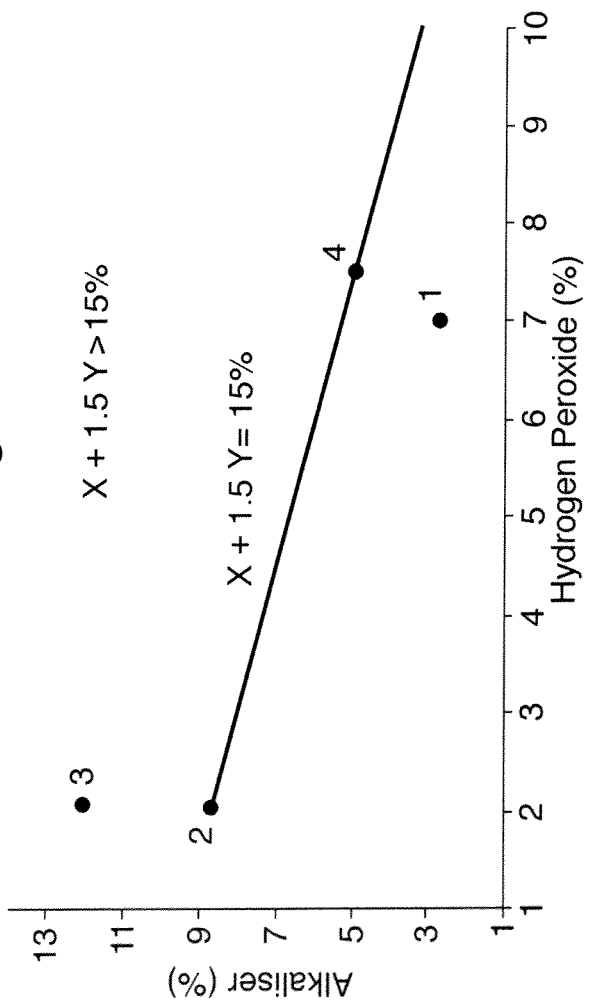

US 8,550,095 B2

SYSTEM FOR HIGHLIGHTING HAIR

CROSS REFERENCE TO RELATED APPLICATION

This application is a divisional application of prior U.S. application Ser. No. 12/135,280 filed Jun. 9, 2008 now U.S. Pat. No. 8,132,570.

FIELD OF THE INVENTION

The present invention relates to a system for highlighting hair with a composition and with a device comprising two movably joined portions.

BACKGROUND OF THE INVENTION

Hair strands effects, such as highlighting, allow a user to achieve a different look than a full head application.

One known method for providing highlighting is the cap and hook system, whereby a cap with holes is positioned over the head and bundles of hair strands are pulled out from the holes with a hook. The highlighting composition is then applied in an excessive amount over the bundles of hair strands to saturate the hair. At professional salons, experienced stylists prefer foils to the cap and hook system. Once a bundle of hair strands has been selected, it is laid upon a foil and covered with a generous amount of highlighting composition to saturate the hair. The process is completed by wrapping the bundle of hair strands within the foil.

Both processes described above are difficult if self-performed and many users still prefer to visit professional salons to achieve a satisfactory result. To facilitate the application of a composition to highlight the hair at home, different devices have been developed. These devices belong within two general fields. One field comprises devices based on combs and/or brushes; the other field encompasses devices comprising two movably joined portions, such as two plates, a plate and a well or two wells. Such devices are characterized by having a first portion, which is for receiving a composition to highlight the hair, and a second portion which is movably joined to the first portion and may be brought into a juxtaposed relationship to the first portion. Non-woven, sponges, foams and other fibrous material may be attached to any of those portions in order to partially absorb the composition to highlight the hair and/or to avoid leakage of the composition outside the device. Usually the application of the composition to highlight the hair is performed by positioning a bundle of hair strands between the movably joined portions and clamping the bundle of hair strands within the devices by bringing the two portions into a juxtaposed relationship. The application is then completed by swiping the devices once or twice along the entire length of the bundle of hair strands.

Some examples of these devices are disclosed in the art such as in: U.S. Pat. Nos. 3,030,968; 6,062,23; 7,025,069; GB 2242357; JP 1999178630; JP 2001211925 and EP 1433399.

Although potentially precise, cheap and user-friendly, these devices apply an amount of composition to highlight the hair which is at least three times less than the amount applied with the cap and hook or the foil system. Consequently, commercially available compositions to highlight the hair used in combination with these devices may not provide the results that a user would reasonably expect.

Thus, what still remains to be solved in the art is to provide a composition to highlight the hair with a device comprising two movably joined portions.

It has now been found that a system (as defined hereafter) is capable of overcoming the technical problem defined above.

SUMMARY OF THE INVENTION

According to the invention, a system for treating the hair is provided, said system comprising a device (10) and a composition (50); wherein said device (10) comprises a first portion movably joined by a connection (30) to a second portion; wherein said composition (50) comprises a percentage X of hydrogen peroxide by weight of said composition (50) and a percentage Y of an alkalizer by weight of said composition (50); wherein said composition (50) comprises a minimum of 2% of hydrogen peroxide by weight of said composition (50); and wherein said weight percentages of said hydrogen peroxide and said alkaliser in said composition (50) are as defined by equation (I); wherein equation (I) is $$X+1.5Y \geq 15\% \qquad (I);$$

wherein said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof.

Furthermore, a method to apply a composition (50) with a device (10) to a hair strand and a kit comprising one or more devices (10) and individually packaged components to form a composition (50) are described. Finally, the use of a composition (50) according to the invention to highlight a hair strand with a device (10), wherein said device (10) comprises a first portion movably joined to a second portion is described.

BRIEF DESCRIPTION OF THE DRAWINGS

FIG. 3B is a view of said internal surface (121) of said plate (120) of said device (10) shown in FIG. 3A. Axis Y extends straight from the centre of said plate (120) and crosses transversally said connection (30). A first fin (70) and a second fin (71) project independently from said internal surface (121). Both proximal edges (90; 91) extend parallel to said axis Y.

FIG. 3C is a cross-section taken perpendicular to axis Y at the centre of said plate (120) shown in FIGS. 3A and 3B. Substantially identical fins (70; 71) project from said internal surface (121) and form with the latter two substantially identical angles α and β. Said fins (70; 71) extend with substantially identical average lengths (L1; L2) and their distal edges (80; 81) verge one toward the other.

FIG. 4 shows a perspective view of an embodiment of device (10) comprising a first portion movably joined by a connection (30) to a second portion. Said composition (50) is loaded in one of said portions.

FIG. 5 shows the relationship defined by equation (I) between the percentage X of hydrogen peroxide and the percentage Y of an alkalizer as described herein within said composition (50). The data points specifically referred in the description are indicated by the correspondent numbers given herein.

DETAILED DESCRIPTION OF THE INVENTION

Figure 1:
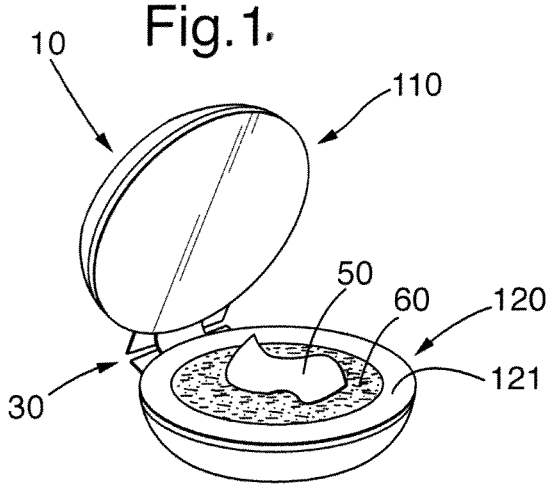
FIG. 1 is a perspective view of the system according to the invention comprising said device (10) and said composition (50). In this embodiment, said device (10) comprises a plate (110) movably joined via a connection (30) to another plate (120). Said latter plate (120) comprises an internal surface (121) on which a material (60) is laid upon. The composition (50) is shown here loaded upon the material (60).

For the purpose of this invention, the term hair refers to both living hair i.e. on a living body and to non-living hair i.e. in a wig, hairpiece or other aggregation of non-living keratinous fibre. Mammalian, preferably human hair is intended.

For the purpose of this invention, the term "hair strand" means a single keratinous fibre, and the term "bundle of hair strands" means a plurality of hair strands according to the meaning given herein.

The present invention is characterized by the synergistic relationship that the features as described herein have when combined together in the specific relationship selected within the present invention to solve the above technical problem.

The system to treat the hair according to the present invention comprises a device (10) and a composition (50). Said device (10) comprises a first portion movably joined to a second portion; said first portion of said device (10) may be either a plate (110) or a well (115), preferably said first portion is a well (115); said second portion of said device (10) may either be a plate (120) or a well (125), preferably said second portion of said device (10) is a plate (120). When said first portion is a well (115), preferably, said well (115) comprises a base (116), a wall (117) and a rim (118). Said base (116), wall (117) and rim (118) define an opening (203) and an internal volume (204) of said well (115). Said internal volume (204) is preferably for containing said composition (50). Preferably, when said second portion is a plate (120), said plate (120) comprises a perimeter (103), and an internal (121) and an external (122) surface. Said internal surface (121) of said plate (120) may be brought into a juxtaposed relationship to said opening (203) of said well (115). Preferably, at least one member (40) or a first fin (70) projects from said internal surface (121) of said plate (120). More preferably, a first (70) and a second (71) fin project from said internal surface (121) of said plate (120). A material (60) selected from the group consisting of non-wovens, foams and combinations thereof may be preferably laid upon said first and/or second portion. More preferably said material (60) is laid upon said rim (118) of said wall (117) of said well (115). Even more preferably said material (60) is laid upon said rim (118) of said wall (117) of said well (115) and also on said perimeter (103) on said internal surface (121) of said plate (120).

Said composition (50) comprises a percentage X of hydrogen peroxide by weight of said composition (50) and a percentage Y of an alkalizer by weight of said composition (50). Said composition (50) comprises at least a minimum of about 2% of hydrogen peroxide by weight of said composition (50). The weight percentages of said hydrogen peroxide and said alkalizer in said composition (50) are as defined by equation (I):

$$X+1.5Y \geq 15\% \quad (I);$$

Said alkalizer comprised within composition (50) is an inorganic salt selected from the group consisting of sodium silicate, sodium metasilicate, potassium hydrogen carbonate, ammonium carbonate, ammonium hydrogen carbonate and sodium hydrogen carbonate and mixtures thereof. Alternatively said alkalizer may be an organic salt.

Commercially available compositions to highlight the hair are suggested to be applied thoroughly and throughout the selected bundle of hair strands. If using a brush, a comb or even the fingers, such self-application may be reasonably easy but presumably not clean or precise or quick to dry after application. If using a device (10), which comprises two movably joined portions, it is possible to apply a composition (50) in a precise manner, so that the application may be performed at home in a clean and tidy fashion. Such a device (10), although cheap, light and user-friendly, suffers a major drawback. This drawback relates to the amount of composition that such a device (10) is capable of applying to a hair strand, preferably to a bundle of hair strands. The present inventors have found that with such a type of device (10), of which three embodiments are shown in FIGS. 1 to 3, the amount of a composition to highlight the hair applied in grams per gram of hair is from about 0.5 grams to about 1.0 gram. This also enables the perceived rate of drying to increase.

A device (10) was manufactured as follows. A piece of cardboard, having a length of about 10 cm and a width of about 5 cm was folded substantially in the middle of its length to obtain a first portion movably joined by a connection (30) to a second portion. Said first and second portions could be brought into a juxtaposed relationship. Said first and second portion each had a surface area of about 25 cm². A non-woven, Libeltex 01-766 DI-8, measuring about 5 cm in length and width was laid upon each of those juxtaposable sides of said first and second portions. The non-woven Libeltex 01-766 DI-8 pieces were attached using double sided adhesive tape (3M™ 465). This device (10) was used to assess what amount of a hair highlighting composition may be applied via said device (10) to a bundle of hair strands. About 4 grams of Revlon™ Custom Effects™ H10 (Revlon™, as purchased in the US in June 2007) was loaded on one of said portions over the non-woven Libeltex 01-766 DI-8. A bundle of hair strands of about 0.30 grams and about 30.5 cm long (Caucasian Light Brown—International Hair Imports and Products, Valhalla, N.Y.) was held together at the top by glue and a cable tie. The bundle of hair strands was located between said movably joined first and second portions on those juxtaposable sides covered by a non-woven Libeltex 01-766 DI-8. Upon bringing said first and second portions into a juxtaposed relationship, said device (10) was swiped along the length of said bundle of hair strands. The swiping was repeated twice. The amount of composition applied to said bundle of hair strands was calculated as the difference in weight of said bundle of hair strands before and after the application of said composition. The experiment was repeated three times and the results were averaged so to obtain an average on-hair dosage. The latter resulted to be about 0.8 grams of composition per gram of hair.

Almost all the compositions commercially available to highlight the hair comprise hydrogen peroxide and an alkalizer Nevertheless, the weight percentages of hydrogen peroxide and of the alkalizer comprised within these commercially available compositions are not contemplated to be applied to the hair in amounts of from about 0.5 grams of composition per gram of hair to about 1.0 gram of composition per gram of hair.

The same composition as used above (Revlon™ Custom Effects™ H10) to measure the average on-hair dosage achieved by a device (10) and referred hereafter as test composition was prepared as prescribed by the manufacturer. A component comprising hydrogen peroxide and a component comprising an alkalizer were mixed together to obtain a test composition comprising about 7% of hydrogen peroxide by weight of said test composition. The amount of alkalizer was estimated to be about 2.7% by weight of said test composition (FIG. 5 data point (1)). An amount of about 1.2 grams of said test composition was evenly applied to a bundle of light brown hair strands of about 1.5 grams (International Hair Imports and Products, Valhalla, N.Y.) so that 0.8 grams of test composition was applied per gram of hair. The bundle of hair strands was left for 30 minutes at 30° C. The bundle of hair strands was then rinsed with water for one minute and air dried for 24 hours. This experiment was repeated on two different bundles of hair strands. Average colour measurements were made by recording and averaging 6 measurements on each bundle of hair strands using a Minolta Spectrophotometer CM-3600d (Integrating sphere, D65 Standard, 10° Observer) to obtain the Lightness values (L). The Lightness values obtained before (A) and after (B) application are reported in table 1. The same experiment was repeated again but an amount of about 6 grams of test composition was applied to a bundle of hair strands of about 1.5 grams, so that about 4 grams of test composition were applied per gram of hair. This roughly represents the amount of test composition which may be applied to the hair with the cap and hook system or foil system. The Lightness values obtained before (C) and after (D) application are also reported in table 1.

Lightness, or L, is a measure of lightness/darkness used within the CIE 1976 (L*a*b) color space otherwise known as CIELAB color space. The L scale extends from 0 for black to 100 for white. The value L is used as a parameter to measure the lightness of the hair and hence allows the quantification of different compositions to highlight the hair. The difference in L values measured on untreated hair and after application of the composition provides a ΔL, which measures the amount of lightening that the composition has provided in a defined period of time. ΔL is provided by equation (II):

$$\Delta L = L(\text{after application}) - L(\text{untreated hair}) \quad \text{(II)}$$

The higher the value of ΔL, the greater the degree and the visibility of the lightening obtained. The degree of lightening is also often referred to by those skilled in the art in terms of "level of lift". Users of compositions to highlight hair typically expect a lightening, on light brown hair, of at least 14 ΔL.

TABLE 1

ΔL values for different amounts of composition applied per gram of hair.

| Application | L (untreated hair) | L (after application) | ΔL |
|---|---|---|---|
| about 0.8 grams/gram of hair | A 33.8 | B 45.0 | 11.2 |
| about 4.0 grams/gram of hair | C 33.9 | D 57.4 | 23.5 |

As can be appreciated from table 1, when a standard commercially available composition such as said test composition is applied in an amount of 0.8 grams per gram of hair, the ΔL value obtained reflects that this type of composition does not provide for a sufficiently noticeable lift of about 14 ΔL.

Although a very subtle lift may be what certain users expect, most of the users, aim to achieve a noticeable or bold lift, especially if they highlight their hair for the first time. A noticeable highlight corresponds to a change in L value of about 3 units more versus what can be obtained, for instance, with a standard commercially composition as referred above.

The present inventors have surprisingly found that a very specific mathematical relationship regulates the percentages of the hydrogen peroxide and of an alkalizer by weight of said composition (50) for providing the expected end result when said composition (50) is delivered in amounts of from about 0.5 grams to about 1.0 gram per gram of hair.

This mathematical relationship is represented by equation (I):

$$X + 1.5Y \geq 15\% \quad \text{(I);}$$

wherein X is the percentage of hydrogen peroxide by weight of said composition (50) and wherein Y is the percentage of an alkalizer by weight of said composition (50).

The present inventors have also surprisingly found that to obtain the technical effect described herein said alkalizer should not only be present in said percentage Y by weight of said composition (50) but also said alkalizer should be an inorganic salt selected from the group consisting of sodium silicate, sodium metasilicate, potassium hydrogen carbonate, ammonium carbonate, ammonium hydrogen carbonate and sodium hydrogen carbonate and mixtures thereof.

The present inventors have also found that at least about 2% of hydrogen peroxide by weight of said composition (50) needs to be present. Without wishing to be bound by theory it is believed that when hydrogen peroxide is present at less than about 2% by weight of said composition (50), to provide at least a noticeable lift on untreated hair, the required percentage of an alkalizer by weight of said composition (50) would shift the pH of said composition (50) to very basic values. Compositions to highlight the hair have preferably a pH of about 9.5 to about 10.5, more preferably about 9.7 to about 10.4. An increase in pH over about 10.5 is likely to damage the hair causing fiber breakage, poor wet feeling after highlighting, poor combing and poor shine. In addition, although a percentage of hydrogen peroxide above about 12% by weight of said composition (50) may provide a noticeable or bold lift, having a component prior to mixing comprising hydrogen peroxide at levels of above about 12% by weight of said component is commercially not practicable. Thus, said composition (50) comprises from about 2% to about 11% of hydrogen peroxide by weight of said composition (50), preferably from about 2% to about 10% of hydrogen peroxide by weight of said composition (50).

Table 2 herein below shows a few examples of compositions (50) and the percentages of hydrogen peroxide and of an alkalizer by weight of said composition (50) which required according to equation (I) to obtain a lift of at least 14 ΔL. Said compositions (50) as indicated in table 2 were mixed to visual homogeneity and each was applied in an amount of about 1.2 grams immediately after mixing to a bundle of hair strands weighing about 1.5 grams (International Hair Imports and Products, Valhalla, N.Y.). The amount of composition (50) applied was thus 0.8 grams per gram of hair.

These three compositions (50) as shown in table 2 further comprised a percentage of ammonium persulfate and of potassium persulfate of about 12% by weight of said composition (50). The ratio between said ammonium persulfate and said potassium persulfate was about 15:85.

TABLE 2

Examples of composition (50) and the percentages of hydrogen peroxide, alkalizer and persulfate by weight of said composition (50) to obtain a lift of at least 14 ΔL.

|     | (X + 1.5Y) | hydrogen peroxide (X) | alkalizer (Y) | persulfate | ΔL |
| --- | --- | --- | --- | --- | --- |
| (2) | 15% | 2% | 8.66% | 12% | 16 |
| (3) | 20% | 2% | 12% | 12% | 17 |
| (4) | 15% | 7.5% | 5% | 12% | 14 |

When the percentage of hydrogen peroxide is about 2% by weight of said composition (50), the percentage of an alkalizer should be at least about 8.66% by weight of said composition (50) as indicated in table 2 and shown in FIG. 5, data point (2). Clearly, by increasing the percentages of an alkalizer by weight of said composition (50) higher than about 8.6% as shown in FIG. 5 data point (3), said composition (50) may provide for a higher lift as indicated in table 2, data point (3), wherein the peroxide concentration is about 2% and the alkalizer concentration is about 12%.

To decrease the percentage of an alkalizer by weight of said composition (50) and still obtaining at least a noticeable level of lift, it is necessary to increase the percentage of hydrogen peroxide by weight of said composition (50) according to equation (I). Thus, if about 5% of an alkalizer by weight of said composition (50) is desired, then at least about 7.5% of hydrogen peroxide by weight of said composition (50) should be included as shown in FIG. 5, data point (4). The lift expressed in ΔL values of highlighted versus untreated hair is indicated in table 2, data point (4).

Preferably said composition (50) comprises a percentage of hydrogen peroxide by weight of said composition (50) plus 1.5 times a percentage of an alkalizer by weight of said composition (50) which at least about 17%, more preferably at least about 20%, even more preferably more than about 20% by weight of said composition (50).

Said composition (50) according to the invention, preferably, comprises from about 3% to about 12% of an alkalizer by weight of said composition (50), more preferably from about 4% to about 10%, even more preferably from about 5% a to about 9% by weight of said composition (50). Said composition (50) according to the invention, preferably comprises from about 2% to about 11% of hydrogen peroxide by weight of said composition (50) more preferably from about 3% to about 11%, even more preferably from about 3% to about 9% by weight of said composition (50).

Composition to Highlight the Hair

1. Hydrogen Peroxide

The hydrogen peroxide used in the composition (50) is preferably provided as an aqueous solution with additives to provide enhanced stability. Suppliers include the Solvay Group who sell hydrogen peroxide at weight percentages of 35%, 50%, 60% and 70% active hydrogen peroxide.

2. Alkalizer

The alkalizer present within said composition (50) is an inorganic salt selected from the group consisting of sodium silicate, sodium metasilicate, potassium hydrogen carbonate, ammonium carbonate, ammonium hydrogen carbonate and sodium hydrogen carbonate or mixtures thereof.

Preferably, said alkalizer comprised within said composition (50) according to the present invention is a mixture of sodium silicate and a salt of hydrogen carbonate. More preferably said mixture comprises a ratio of said sodium silicate to said salt of hydrogen carbonate of from about 90:10 to about 60:40, more preferably from about 85:15 to about 70:30.

Also, preferably said alkalizer comprises a mixture of sodium silicate and sodium metasilicate.

Additional inorganic salts which may be optionally present within said composition (50) include, but are not limited to, sodium chloride, aluminum citrate, calcium saccharin, calcium salicylate, calcium citrate, calcium benzoate, magnesium acetate, magnesium ascorbate, ammonium chloride, magnesium gluconate, potassium acetate, potassium benzoate, potassium citrate, potassium sorbate, sodium acetate, sodium ascorbate, sodium citrate, sodium gluconate, sodium pyruvate, sodium carbonate, magnesium carbonate, and mixtures thereof.

3. Additional Components

The composition (50) according to the invention may further comprise a persulfate salt. Said persulfate salt is selected from the group consisting of ammonium persulfate, sodium persulfate, potassium persulfate and mixtures thereof. Preferably, said composition (50) comprises at least about 2%, more preferably at least about 4% and even more preferably at least about 6% of said inorganic persulfate by weight on said composition (50).

Preferably said persulfate salt comprises a mixture of ammonium persulfate and potassium persulfate. More preferably, the ratio within said mixture between said ammonium persulfate and said potassium persulfate is from about 5:95 to about 50:50, even more preferably from about 10:90 to about 25:75.

Said composition (50) may further comprise components known, conventionally used, or otherwise effective for use in hair treatment compositions particularly oxidative bleaching and dye compositions which include but are not limited to: developer dye compounds; coupler dye compounds; direct dyes; For example, D&C Orange 4, Acid Yellow 1, D&C Red No. 28, Disperse Red 17, HC Blue No. 15, Acid Blue; oxidizing agents; reducing agents; one or more thickeners; chelants; pH modifiers and buffering agents; alkalising agents, carbonate ion sources and radical scavenger systems; glycine; amodimethicone; ethylenediamine disuccinic acid; anionic, cationic, non-ionic, amphoteric or zwitterionic surfactants, or mixtures thereof; anionic, cationic, non-ionic, amphoteric or zwitterionic polymers, hydrophobically modified polymers or mixtures thereof; fragrances; dispersing agents; solvents, peroxide stabilizing agents; chelants, humectants, proteins and derivatives thereof; plant materials (e.g. aloe, chamomile and henna extracts); silicones (volatile or non-volatile, modified or non-modified), film-forming agents, oleogels, cellulose polymers and their derivatives, ceramides, preserving agents, gel networks, one or more colour indicators and opacifiers including titanium dioxide and ultramarines. Some adjuvants which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A representative but not exhaustive list of polymers and thickening agents can be found in "The Encyclopaedia of Polymers and Thickeners for Cosmetics" compiled and edited by Robert Y. Lochhead, PhD and William R. Fron, Department of Polymer Science, University of Southern Mississippi.

Device

The system according to the present invention comprises a device (10). Said device (10) comprises a first portion movably joined to a second portion. Said first portion may be either a plate (110) or a well (115), preferably said first portion is a well (115). Said second portion may be either a plate (120) or a well (125), preferably said second portion is a plate (120).

Said plate (120) and said well (115) of said device (10) according to the invention are of ergonomic size and can thus fit easily on either hand. The shape of said plate (120) may vary. Rectangular, square, circular, elliptical, oblong shape or combination thereof may be useful as they are easy to manufacture but other shapes, particularly those that are easily recognized by the consumers may also be used.

Said plate (120) comprises a perimeter (103), an internal surface (121) and an external surface (122). Said well (115) comprises a base (116), a wall (117) and said wall (117) comprises a rim (118). Said base (116), said wall (117) and said rim (118) define an opening (203) and an internal volume (204) of said well (115), wherein said internal volume (204) is preferably for containing said composition (50). Said perimeter (103) of said plate (120) and the rim (118) of said wall (117) of said well (115) may be curvilinear or sharp. Irrespectively from their shape, preferably said perimeter (103) of said plate (120) has substantially the same extension of said rim (118) of said well (115).

Said internal surface (121), said external surface (122) of said plate (120) as well as said base (116) and said wall (117) of said well (115) may further comprise one or more areas, which have visible and/or tactile differences from said internal surface (121) and/or from said external surface (122) and/or from said bottom (116) and/or from said wall (117). Said visible or tactile differences comprise differences in colour and/or shade, differences in patterns, markings and/or embossments. Those visible or tactile differences, differences in colour and/or shade, differences in patterns, markings and/or embossments, in particular those present in the well (115) may be provided to indicate where and how much composition (50) should be loaded into said device (10).

Said internal surface (121) of said plate (120) is preferably substantially flat whilst said external surface (122) of said plate (10), said base (116) and said wall (117) of said well (115) may be independently substantially flat or curved. Preferably, said base (116) of said well (115) is substantially flat. When said internal surface (121) is substantially flat, it preferably has a surface area of from about 2 $cm^2$ to about 150 $cm^2$, preferably from about 2 $cm^2$ to about 70 $cm^2$, more preferably from about 3 $cm^2$ to about 50 $cm^2$, even more preferably from about 4 $cm^2$ to about 30 $cm^2$.

Said plate (120) and/or said well (115) or at least a portion thereof may comprise one or more cavities, one or more V- or U-shaped grooves or combinations thereof. Said cavities or grooves may be independently located on said internal surface (121), on said external surface (122), on said base (116), on said wall (117) or combinations thereof.

Said plate (120) and said well (115) may be manufactured from any known material including; polyolefins, acrylonitrile butadiene styrene, where appropriate; flexible pliable substrates such a paper boards, and polycarbonate among others and combinations therefore. Useful methods of manufacture may include injection moulding, co-injection moulding and vacuum forming among others and combinations thereof.

A material (60) may be laid upon said first and/or second portion of said device (10). Said material (60) is preferably selected from the group consisting of non-wovens, foams and combinations thereof. One embodiment is shown in FIG. 1, wherein a disk of material (60) is laid upon said internal surface (121) of said plate (120). Another embodiment is shown in FIG. 4 wherein a non-woven Libeltex 01-766 DI-4 is laid upon both said first and second movably joined portions. Preferably, a non-woven Libeltex 01-766 DI-8 is laid upon said rim (118) of said wall (117) of said well (115), even more preferably said non-woven Libeltex 01-766 DI-4 is laid upon said internal surface (121) of said plate (120) along said perimeter (103).

Said material (60) may be removable or permanently laid upon said first and/or second portions of said device (10). Any methods suitable to attach said material (60) may be employed herein providing that said method does not destroy or alter the performance of said material (60). Useful methods to attach said material (60) include heat welding, adhesive and extrusion lamination among others and combinations thereof. Preferably said material (60) is laid upon both of said first and second portions of said device (10), such that when said device (10) is in a closed state, the first and second portions comprising said material (60) are substantially juxtaposed. The presence of said material (60) improves the evenness of the application of the hair treatment composition and reduces dripping out of the device (10)

Said first and second portion of said device (10) are movably joined. Said first and second portion may be movably joined through a connection (30). Preferably, a connection (30) movably joins said plate (120) and said well (115). A connection (30) is necessary in the device (10) to improve the user's perception of control over the device (10) and to allow the user to guide the device (10), with the use of either hand, precisely and easily to each bundle of hair strands.

Figure 2A:
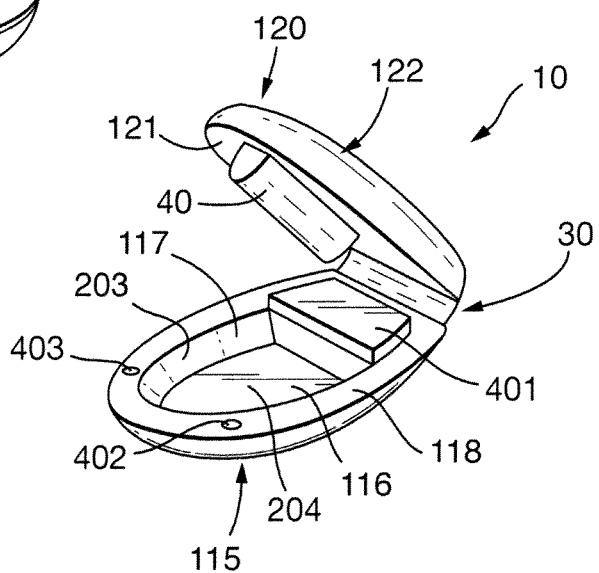
FIG. 2A is a perspective view of an embodiment of said device (10) according to the invention. A plate (120) is movably joined to a well (115) by a connection (30). The well (115) comprises a base (116), a wall (117) and a rim (118) which altogether define an opening (203) and an internal volume (204) of the well (115). A sealing means (401) is located on a portion of the base (116) contiguous to the wall (117) on one side of the connection (30). Two stop mechanisms, in this embodiment represented by two substantially identical hemispheres (402; 403) are located on the rim (118). Said plate (120) comprises an external surface (122) and an internal surface (121) and a member (40) projects from said internal surface (121) of said plate (120).
Figure 2B:
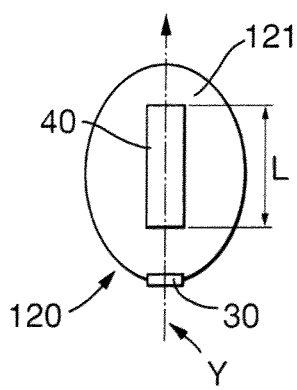
FIG. 2B is a view of the internal surface (121) of said plate (120) of said device (10) shown in FIG. 2A. Axis Y extends straight from the centre of said plate (120) and crosses transversally said connection (30), preferably perpendicular to said connection (30). A member (40) extends with its maximum length (L) along said internal surface (121).
Figure 2C:
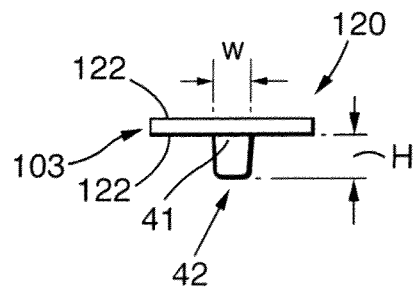
FIG. 2C is a cross-section taken perpendicular to axis Y at the centre of said plate (120) shown in FIG. 2B. Said plate (120) comprises a perimeter (103), an external surface (122) and an internal surface (121) from which a member (40) projects with maximum height (H) and extends along said internal surface (121) with maximum width (W). Said proximal (41) and distal (42) bases are also shown.
Figure 3A:
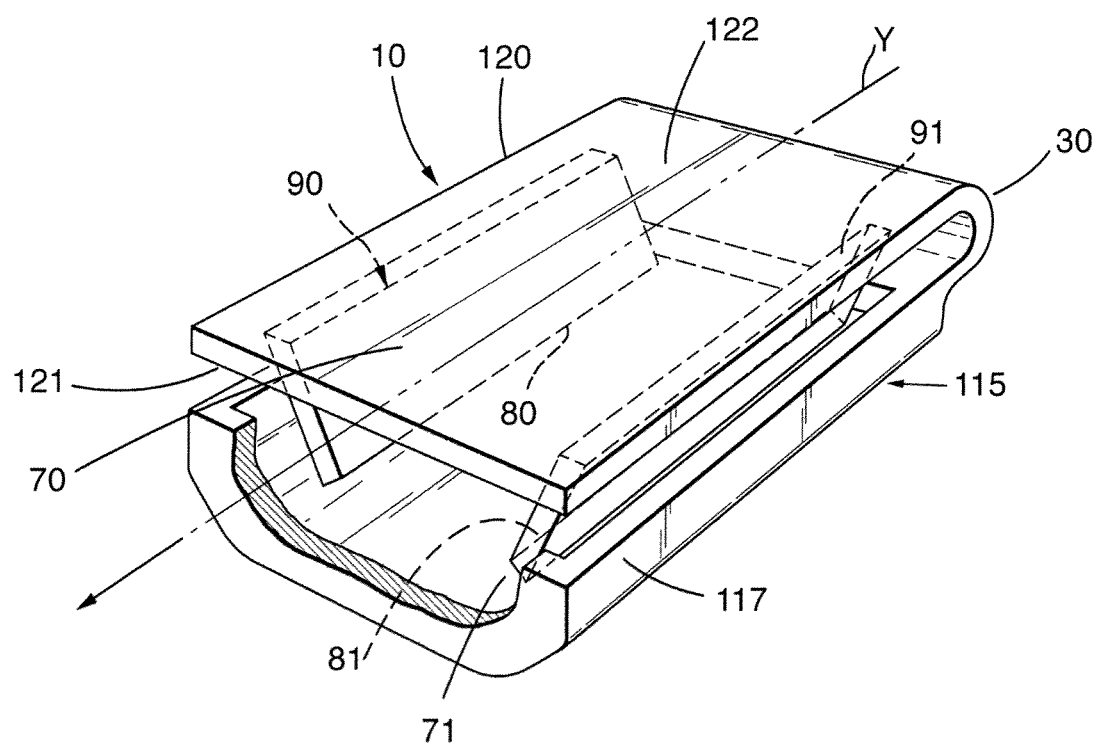
FIG. 3A is a perspective view of a device (10) according to the invention, said device (10) comprising a plate (120) a well (115) movably joined by a connection (30) to said plate (120), which comprises an axis Y and has an internal (121) and an external (122) surface. Said internal surface (121) of said plate (120) is in a juxtaposed relationship to said opening (not shown herein) of said well (115). Part of said wall (117) of said well (115) has been removed to show a first (70) and a second (71) fin. The first fin (70) and the second fin (71) project independently from said internal surface (121) of said plate (120). Each of said fins (70; 71) comprises a distal edge (80; 81) and a proximal edge (90; 91). Said proximal edges (90; 91) are those attached to said internal surface (121) of said plate (120), whist said distal edges (80; 81) in this embodiment verge one toward the other.

Being said plate (120) and said well (115) movably joined and having a connection (30) between said plate (120) and said well (115) it is possible for said device (10) to alternate from an open state to a closed state. Said device (10) is shown in FIGS. 1 and 2 in an open state. When said device (10) is in a closed state, as shown in FIG. 3A, said internal surface (121) of said plate (120) is in a juxtaposed relationship to said opening (203) of said well (115). Said plate (120) and said well (115) may pivot about said connection (30) to alternate from an open state to a closed state; in one embodiment, the device (10) is in an open state and the user applies pressure on said external surface (122) of said plate (120) and on said well (115) to bring the device (10) into a closed state. To move said plate (120) and said well (115) back from a close state to a open state either said external surface (122) of said plate (120) and said well (115) may be independently provided with one or more fitting means for the user's fingers or the connection (30) itself may re-establish the initial orientation of said plate (120) and said well (115), preferably by springing back.

The plate (120) and the well (115) are connected via any suitable means that fulfils the above described requirements for the connection (30), including the user's hand, for example through the thumb and index finger. In one embodiment, said plate (120) and said well (115) are mounted at the ends of the arms of a tweezers-like or tong-like connection (30). In another embodiment said plate (120) and said well (115) are connected via one or more hinges, preferably said connection (30) is a hinge.

The device (10) may further comprise one or more sealing means, preferably one sealing means (401) is present within the device (10). Said sealing means (401) may be located within said well (115) on said base (116) at the wall (117) adjacent to said connection (30) as shown in FIG. 2A. Said sealing means (401) may be located on the base (116) of said well (115) adjacent to said wall (117) at the side of the connection (30) or on said internal surface (121) adjacent to said connection (30). Preferably said sealing means (401) is part of said connection (30).

One or more stop mechanisms may be incorporated onto said device (10). The stop mechanism collaborates with said connection (30) to ensure that when said internal surface (121) of said plate (120) is brought into a correct juxtaposed relationship to said opening (203) of said well (115). One or more stop mechanism may reduce forcing said composition (50) beyond said rim (118) of said well (115).

In certain embodiments the stop mechanism may be one or more tines, teeth of a comb-like structure. In one embodiment as shown in FIG. 2A, two stop mechanisms are comprised on said rim (117) of said wall (118) of said well (115), preferably said two stop mechanisms are two substantially identical hemispheres (402; 403). In certain other embodiments, not shown herein, the stop mechanism may be integrated within connection (30) itself.

Useful materials to manufacture a stop mechanism (402) may include those described herein above to manufacture said plate (120) and combinations thereof.

In one embodiment of the present invention, a member (40) projects from said internal surface (121) of said plate (120) as shown in FIG. 2A. Said proximal base (41) is attached to said internal surface (121). Said plate (120) of said device (10) according to the present invention comprises an axis Y. Said axis Y extends substantially straight from the centre of said plate (120) and crosses transversally said connection (30) as shown in FIG. 2B preferably perpendicular to said connection (30. Said member (40) has a maximum length (L) as shown in FIG. 2B. Said member (40) comprises a proximal base (41) and a distal (42) base as shown in FIG. 2C. Said member (40) has a maximum height (H) and a maximum width (W) as shown in FIG. 2C. Said member (40) preferably projects orthogonally to said axis Y with said maximum height (H) from said internal surface (121) of said plate (120). Said member (40) may extend with its maximum length (L) transversally to said axis Y. Said member (40) preferably extends with its maximum length (L) along and/or substantially parallel to said axis Y.

Preferably, said maximum length (L) is at least twice said maximum width (W). The maximum length (L) is preferably from about 20.0 cm to about 0.2 cm, more preferably from about 15.0 cm to about 0.3 cm, even more preferably from about 10.0 cm to about 0.5 cm. The maximum width (W) is preferably from about 2.5 cm to about 0.01 cm, more preferably from about 1.0 cm to about 0.02 cm, even more preferably from about 0.5 cm to about 0.03 cm. The maximum height (H) is preferably from about 5.0 cm to about 0.1 cm, more preferably from about 2.5 cm to about 0.2 cm, even more preferably from about 1.5 cm to about 0.3 cm.

The member (40) may have various forms including, but not limited to, a parallelepiped form, a cube form, a cylinder form, a conical or a pyramidal frustum form. In an embodiment of the present invention shown in FIG. 2A, said member (40) has preferably a substantially pyramidal frustum form.

In another embodiment not show herein, said member (40) comprises a cylinder which is rotary engaged via its circular bases to said internal surface (121) via two pins, emerging from said internal surface (121) of said plate (120).

When said device (10) is in a closed state, said distal base (42) of said member (40) does not contact said base (116) of said well (115), so that a passage is left and said hair strand, preferably said bundle of hair strands, is not constrained.

Whilst not wishing to be bound by theory it is believed that the presence of the member (40) facilitates the insertion of the hair strand within said well (20) by bending the hair strand, thereby contacting the hair strand with said composition (50). This improves the evenness of the application of said composition (50) on said hair strand. Materials to manufacture said member (40) may be selected from those described herein above to manufacture said plate (120). and combinations thereof.

In another embodiment according to the invention said device (10) comprises a first fin (70), preferably a first (70) and a second fin (71), which independently project from said internal surface (121) of said plate (120). The term "fin" within the scope of the present invention defines a strip or sheet of material, preferably of substantially constant thickness as described below. The form of said first (70) and/or second (71) fin may vary; preferably said first (70) and/or second (71) fin have the form of a parallelepiped wherein two of the six faces extends for an area which is at least twice the area of the other four faces. Those two faces have preferably a substantially flat surface. The shape of said first (70) and second (71) fin may vary. Rectangular, square, circular, elliptical, oblong or combination thereof may be useful. A rectangular shape as shown in FIG. 3 is preferred.

Whilst not wishing to be bound by theory it is believed that the presence of said first fin (70) and preferably said second fin (71) also facilitates the insertion of the hair strand within said well (20) by bending the hair strand, thereby contacting the hair strand with said composition (50). This improves the evenness of the application of said composition (50) on said hair strand.

As shown in FIG. 3C, a first fin (70) projects from said internal surface (121) of said plate (120) and extends for an average first length (L1) of from about 1 mm to about 50 mm Said first fin (50) forms with said substantially flat internal surface (101) of said plate (10) and angle α of from about 15° to about 75°. Preferably, when said internal surface (121) of said plate (120) is substantially flat said angle α is from about 35° to about 55°, more preferably from about 35° to about 50°. Preferably, a second fin (71) projects from said internal surface (121) of said plate (120) independently from said first fin (70), as shown in FIGS. 3A, 3B and 3C and extends independently from said first fin (70) for an average second length (L2) of from about 1 mm to about 50 mm Said second fin (71) forms with said internal surface (121) of said plate (120) an angle β of from about 15° to about 75°, independently from said angle α formed by said first fin (70). Preferably, when said internal surface (121) of said plate (120) is substantially flat, said angle β is from about 35° to about 55°, more preferably from about 35° to about 50°. More preferably, said internal surface (121) of said plate (120) is substantially flat and said first fin (70) and said second fin (71) form with said substantially flat internal surface (121) substantially identical angles α and β of from about 35° to about 55°.

Each of said first (70) and second (71) fin has a distal edge (80; 81) and a proximal edge (90; 91). Said proximal edges (90; 91) are those attached to said internal surface (121) of said plate (120) a shown in FIG. 3A. Said proximal edges (90; 91) are each independently delimited by a first average width (W1) for said first fin (70) and a second average width (W2) for said second fin (71) and each independently by a first average thickness (T1) for said first fin (70) and a second average thickness (T2) for said second fin (71). Said first and second average widths (W1) and (W2) are preferably of from about 20 cm to about 0.5 cm, more preferably from about 15 cm to about 1 cm, whereas said first and second average thicknesses (T1) and (T2) are preferably from about 5 mm to about 0.1 mm, more preferably from about 4 mm to about 0.5 mm. Preferably, said proximal edges (90; 91) have substantially identical first and second average widths (W1; W2) and substantially identical first and second average thicknesses (T1; T2). Said distal edges (80; 81) of said first and second fins (70; 71) preferably have substantially identical dimensions to said proximal edges (90; 91).

According to the present invention, when a first (70) and a second (71) fin are present, it is irrespective which of those two fins is named first fin (70) or second fin (71). When said device (10) comprises only one fin, said fin is called first fin (70) and when said device (10) comprises two fins, said fins which comprises the longest average width is called first (70) fin.

Said first and second fin (70; 71) may project from said internal surface (121) of said plate (120) in any orientation one with respect to the other. Preferably, said first (70) and second (71) fin project from said internal surface (121) so that said proximal edge (90) of said first fin (70) is substantially parallel to said proximal edge (91) of said second fin (71) as shown in FIG. 3A. Preferably said proximal edge (90) of said first fin (71), more preferably said proximal edge (90) of said first fin (71) and said proximal edge (91) of said second fin (71) project from said internal surface (121) parallel to said axis Y of said plate (120) as shown in FIGS. 3A and 3C.

When the device (10) comprises a first and a second fin (70; 71), said distal edge (80) of said first fin (70) and distal edge (81) of said second fin (71) may verge one toward the other as shown in FIG. 3B or may diverge toward opposite direction or they may point toward the same direction without verging.

One preferred embodiment of said device (10) according to the invention comprises a first fin (70) and a second fin (71), said first and second fins (70; 71) extend independently for substantially identical average lengths (L1) and (L2), said internal surface (121) of said plate (120) is substantially flat and said first fin (70) and said second fin (71) form with said substantially flat internal surface (121) substantially identical angles α and β of from about 35° to about 55°, and said first and second fin (70; 71) project from said internal surface (121) of said plate (120) such that said distal edges (80; 81) verge one toward the other as shown in FIG. 3A.

Said first and second fin (70; 71) may be provided in a variety of materials and include those described herein above for said plate (120), and polytetrafluoroethylene, latex, thermo plastic elastomer and combinations thereof. Preferably the material is flexible.

Method of Use

The present invention also relates to a method to apply a composition (50) to a hair strand, preferably a bundle of hair strands, whereby said hair strand is contacted with said device (10) as described herein. Said device (10) may be pre-loaded with said composition (50), but preferably said composition (50) is loaded into said device (10) before contacting said hair strand, preferably said bundle of hair strands, with said device (10).

The hair treatment composition can be loaded onto the device (10) by any means. In one embodiment the hair treatment composition is loaded directly into said internal volume (204) of said well (115) by applying said composition (50) for example with a spatula or a syringe, by a squeezable tube, by a dispensing bottle, by a single or dual phase pump, by a single or dual phase piston causing volumetric displacement, by a sachet or by any other suitable dispenser.

Once said device (10) is loaded with said composition (50), the user holds said device (10) through the external surfaces (122) of said plate (120) and of said well (115) in one hand, preferably between the thumb and the index finger. Once the user has selected the hair strands to be treated, said hair strand, preferably said bundle of hair strands, is located between said plate (120) and said well (115) while said device (10) is in an open state. Subsequently said device (10) is brought into a closed state by bringing said internal surface (121) of said plate (120) into a juxtaposed relationship to said opening (203) of said well (115). While kept in a closed state said device (10) is swiped along the length of said hair strand to apply said composition (50). More preferably said device (10) is located at the root-line of said hair strand, preferably at the root-line of said bundle of hair strands. Said composition (50) may also be applied only to limited areas of the hair, i.e. the user can coat only the root-line with the hair treatment composition. The swiping may be repeated more than once, preferably twice. Said composition (50) is optionally rinsed off with water and or shampoo and then styled and or dried as required.

Said composition (50) may be used to highlight a hair strand, preferably a bundle of hair strands, with a device (10), wherein said composition (50) comprises a percentage Y of an alkalizer by weight of said composition (50) and a percentage X of hydrogen peroxide by weight of said composition (50); wherein said composition (50) comprises a minimum of 2% of hydrogen peroxide by weight of said composition (50); wherein the weight percentages of said hydrogen peroxide and said alkalizer are as defined by the equation (I) or more; wherein equation (I) is:

$$X+1.5Y\geq 15\% \qquad (I);$$

wherein said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof.

Preferably, said composition (50) has a rheology of from about 10 Pa to about 160 Pa, more preferably of from about 12 Pa to about 120 Pa, most preferably from 15 Pa to 80 Pa at 1.0 $s^{-1}$.

The rheology of the hair treatment composition is measured using a TA Instruments Advanced Rheometer (AR) 2000. The instrument is provided with a concentric cylinder base with an internal radius of 15.00 mm and standard size vane geometry with a radius of 14.00 mm and a height of 42.00 mm. The geometry gap is set at 4000 microns. Hair treatment compositions which are made up of more than one formulation are prepared by mixing those various formulations thoroughly by hand shaking in a sample pot for 30 seconds. The mixed hair treatment composition is then placed immediately into the concentric cylinder base, and the standard vane geometry is lowered to the geometry gap such that the top of the vanes are covered by the hair treatment compositions. The temperature is equilibrated to 25° C., and then hair treatment composition is left for an additional 30 seconds before the shear rate increases logarithmically from about 0.05 to about 200 s$^{-1}$, recording seven points per decade. At all stages the temperature is maintained at 25° C. The shear stress is recorded at 1.0 s$^{-1}$ and reported in Pa.

Kit

The present invention further comprises a kit. Said kit comprises one or more devices (10), wherein said device (10) comprises a first portion movably joined to a second portion; and at least a first and a second individually packaged component to form said composition (50) as described herein. Said first individually packaged component comprises hydrogen peroxide and said second individually packaged component comprises an alkalizer. Said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof.

In one embodiment of the kit according to the present invention said first individually packaged component comprises from about 2% to about 12% of hydrogen peroxide by weight of said first individually packaged component and said second individually packaged component comprises from about 10% to about 60% of an alkalizer by weight of said second individually packaged component, wherein said second individually packaged component is in the form of a powder or paste; wherein said second individually packaged component further comprises about 20% to about 60% by weight of a persulfate salt, wherein said persulfate salt is selected from the group consisting of sodium persulfate, potassium persulfate, ammonium persulfate and mixtures thereof. Said kit may optionally comprise a third or more individually packaged components.

In another embodiment, invention said first individually packaged component comprises from about 2% to about 12% of hydrogen peroxide by weight of said first individually packaged component and said second individually packaged component comprises from about 10% to about 100% of an alkalizer by weight of said second individually packaged component, wherein said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof; wherein said second individually packaged component is in the form of a powder or paste; wherein said kit further comprises a third individually packaged component, wherein said third individually packaged component comprises about 20% to about 95% by weight of a persulfate salt, wherein said persulfate salt is selected from the group consisting of sodium persulfate, potassium persulfate, ammonium persulfate and mixtures thereof and wherein said kit optionally comprises a fourth or more individually packaged component.

Additional individually packaged components may be present in said kit according to the present invention and may comprise shampoo, conditioner or styling products. The kit according to the present invention may further comprise additional components such as means to select the hair strands, combs or brushes, gloves, caps with holes, tweezers, tongues, hooks or combination thereof.

The kit according to the present invention may further comprise instructions for using said device (10), to prepare and/or to apply said composition (50). Said instructions may be recorded in any type of media such as the package of the kit itself, paper material, compact disk, DVD, website address, or the dispensing means and/or the device (10) itself.

EXAMPLES

Herein below in are given some examples of composition (50) which may be loaded into said device (10) according to the invention.

Compositions (50) were formulated by mixing about 45 grams of the hydrogen peroxide phases (E to K) with about 15 grams of the respective alkaliser phases (e to k).

TABLE 3

Examples of compositions according to the invention. Ingredients are in percentages by weight for each individual hydrogen peroxide phase and alkaliser phase which can be mixed together to form said composition (50).

|  | E + e | F + f | G + g | H + h | I + i | J + j | K + k |
| --- | --- | --- | --- | --- | --- | --- | --- |
| X + 1.5 Y = | 15.4 | 17.3 | 17.6 | 15.8 | 17.6 | 20.6 | 17.3 |
| Hydrogen peroxide (X) | 2.25 | 2.25 | 4.50 | 4.50 | 4.50 | 6.75 | 6.75 |
| Alkaliser (Y) | 8.75 | 10.00 | 8.75 | 7.50 | 8.75 | 9.25 | 7.00 |
| Ingredients | E | F | G | H | I | J | K |
| water | qs. 100% | qs. 100% | qs. 100% | qs. 100% | qs. 100% | qs. 100% | qs. 100% |
| hydrogen peroxide (35% active) | 8.57 | 8.57 | 17.14 | 17.14 | 17.14 | 25.71 | 25.71 |
| cetearyl alcohol[10] | 3.50 | 3.50 | 3.50 | 3.50 | 3.50 | 3.50 | 3.50 |
| ceteareth-25[5] | 1.0 | 1.00 | 1.00 | 1.00 | 1.00 | 1.00 | 1.00 |
| salicylic acid | 0.10 | 0.10 | 0.10 | 0.10 | 0.10 | 0.10 | 0.10 |
| disodium diphosphate | 0.10 | 0.10 | 0.10 | 0.10 | 0.10 | 0.10 | 0.10 |
| phosphoric acid | 0.10 | 0.10 | 0.10 | 0.10 | 0.10 | 0.10 | 0.10 |
| etidronic acid | 0.01 | 0.01 | 0.01 | 0.01 | 0.01 | 0.01 | 0.01 |
| Ingredients | e | f | g | h | i | j | k |
| ammonium persulfate | 8.00 | 20.00 | 8.00 | 19.00 | 8.00 | 6.00 | 10.00 |
| potassium persulfate | 48.00 | 31.00 | 48.00 | 42.00 | 48.00 | 48.00 | 53.00 |
| EDTA | 1.00 | 1.00 | 1.00 | 1.00 | 1.00 | 1.00 | 1.00 |
| titanium dioxide | 3.00 | 3.00 | 3.00 | 3.00 | 3.00 | 3.00 | 3.00 |
| ultramarine blue | 1.00 | 1.00 | 1.00 | 1.00 | 1.00 | 1.00 | 1.00 |
| sodium silicate | 35.00 | 40.00 | 28.00 | 30.00 | 26.00 | 37.00 | 28.00 |

TABLE 3-continued

Examples of compositions according to the invention. Ingredients are in percentages by weight for each individual hydrogen peroxide phase and alkaliser phase which can be mixed together to form said composition (50).

| | | | | | | | |
|---|---|---|---|---|---|---|---|
| potassium hydrogen carbonate | | | 7.00 | | 9.00 | | |
| Carbomer ™ Ultrez 10 | 4.00 | 4.00 | 4.00 | 4.00 | 4.00 | 4.00 | 4.00 |

A composition (50) was prepared by mixing about 45 g of any of the formulations of Phase 1 (1.1, 2.1, 3.1, 4.1, 5.1, 6.1, 7.1, 8.1 or 9.1, table 4), which were in a liquid form with about 15 g of any of the formulations of Phase 2 (1.2, 2.2, 3.2, 4.2, 5.2, 6.2, 7.2, 8.2 or 9.2 in table 4), which were in a solid form. Mixing was achieved as follows: the solid formulation of Phase 2 was placed into a mixing tray and the liquid formulation of Phase 1 was poured on top of the solid Phase 1. The two formulations were then mixed together using a spatula to form a composition (50) to highlight the hair. Mixing was completed when the composition (50) looked visually homogeneous.

TABLE 4

Formulations of Phase 1 and 2 which can be mixed to form a highlighting composition. All ingredients are in percentage by weight of the formulation phase.

| | 1.1 + 1.2 | 2.1 + 2.2 | 3.1 + 3.2 | 4.1 + 4.2 | 5.1 + 5.2 | 6.1 + 6.2 | 7.1 + 7.2 | 8.1 + 8.2 | 9.1 + 9.2 |
|---|---|---|---|---|---|---|---|---|---|
| X + 1.5Y | 17.6 | 17.6 | 17.6 | 17.6 | 17.6 | 17.6 | 17.6 | 17.6 | 17.6 |
| Hydrogen Peroxide (X) | 4.51 | 4.51 | 4.51 | 4.51 | 4.51 | 4.51 | 4.51 | 4.51 | 4.51 |
| Alkaliser (Y) | 8.75 | 8.75 | 8.75 | 8.75 | 8.75 | 8.75 | 8.75 | 8.75 | 8.75 |
| Phase 1 | 1.1 | 2.1 | 3.1 | 4.1 | 5.1 | 6.1 | 7.1 | 8.1 | 9.1 |
| De-ionized Water | q.s. to 100% | q.s. to 100% | q.s. to 100% | q.s. to 100% | q.s. to 100% | q.s. to 100% | q.s. to 100% | q.s. to 100% | q.s. to 100% |
| Glycerine | 5.00 | | | | | | | | |
| Hydrogen Peroxide (35% Active) | 17.20 | 17.20 | 17.20 | 17.20 | 17.20 | 17.20 | 17.20 | 17.20 | 17.20 |
| Disodium EDTA | 0.04 | 0.04 | 0.04 | 0.04 | 0.04 | 0.04 | 0.04 | 0.04 | 0.04 |
| Carbopol ™ 956[1] | 1.00 | | | | | | | | |
| Sodium Hydroxide (50% aq. Solution) | q.s. to pH 3.5 | q.s. to pH 3.5 | q.s. to pH 3.5 | q.s. to pH 3.5 | q.s. to pH 3.5 | q.s. to pH 3.5 | q.s. to pH 3.5 | q.s. to pH 3.5 | q.s. to pH 3.5 |
| Keltrol ™ T[2] | | | 1.25 | | | | | | |
| Stearyl Alcohol[3] | | 2.00 | | 1.00 | 1.00 | 2.00 | 2.00 | 2.00 | 2.00 |
| Cetyl Alcohol[4] | | 3.00 | | 1.50 | 1.50 | 3.00 | 3.00 | 3.00 | 3.00 |
| Ceteareth 25[5] | | 1.50 | | 0.75 | 0.75 | 1.50 | 1.50 | 1.50 | 1.50 |
| Aculyn ™ 33[6] | | | | 2.40 | | | | | |
| Natrosol ™ Plus CS Grade 330[7] | | | | | 1.25 | | | | |
| Salcare ™ SC 90[8] | | | | | | | | 1.00 | |
| Phase 2 Persulfate Powders | 1.2 | 2.2 | 3.2 | 4.2 | 5.2 | 6.2 | 7.2 | 8.2 | 9.2 |
| Ammonium Persulfate | 25.00 | 25.00 | 25.00 | 25.00 | 25.00 | 25.00 | 25.00 | 25.00 | 25.00 |
| Potassium Persulfate | 33.00 | 33.00 | 33.00 | 33.00 | 33.00 | 33.00 | 33.00 | 29.00 | 30.00 |
| Sodium Persulfate | 7.00 | 7.00 | 7.00 | 7.00 | 7.00 | 7.00 | 7.00 | 7.00 | 7.00 |
| Sodium silicate | 35.00 | 35.00 | 35.00 | 35.00 | 35.00 | 35.00 | 35.00 | 35.00 | 35.00 |
| Keltrol T (Xanthan Gum) | | | | | | | | 4.00 | |
| Carbopol ™ Ultrez 10[9] | | | | | | | | | 3.00 |

[1] Carbopol ™ 956, Noveon Inc.
[2] Keltrol ™ T-CP Kelco
[3] Stearyl Alcohol Crodacol S-95, Croda, Inc.
[4] Cetyl Alcohol, Crodacol C-70, Croda, Inc.
[5] Cetearth 25, Cremophor A 25, BASF Corporation
[6] Aculyn ™ 33, Rohm and Hass Company Inc.
[7] Natrosol ™ Plus CS Grade 330, Hercules Incorporated
[8] Salcare ™ SC 90 Ciba Specialty Chemicals Corporation
[9] Carbopol ™ Ultrez 10, Noveon Inc.

In another example, a composition (50) was prepared by mixing into a tray with a spatula 30 g of component (a1), in table 5, comprising hydrogen peroxide with 15 g of component (b1), in table 5, comprising persulfate salts.

TABLE 5

Formulations of components (a1), (a2), All ingredients are indicated in grams.

| Ingredients | |
|---|---|
| | (a1) |
| Water | 78.54 |
| Hydrogen peroxide (35% active) | 17.14 |
| Cetearyl alcohol[10] | 2.25 |
| trideceth 2 carboxamide MEA[11] | 0.85 |
| ceteareth-30[12] | 0.60 |
| glycerin | 0.50 |
| pentasodium pentetate[13] | 0.06 |
| sodium stannate | 0.04 |
| tetrasodium pyrophosphate | 0.02 |
| | (b1) |
| potassium persulfate | 42.80 |
| sodium silicate | 22.50 |
| sodium persulfate | 11.00 |
| acrylates/C10-30 alkyl acrylate crosspolymer[19] | 4.30 |
| Urea | 3.00 |
| Kaolin | 2.90 |
| Magnesium Stearate[20] | 2.80 |
| Ammonium Chloride | 2.60 |
| diethylhexyl sodium sulfosuccinate[21] | 2.00 |
| VP/VA copolymer[22] | 2.00 |
| Polydecene[23] | 1.70 |
| sodium metasilicate | 1.60 |
| EDTA | 0.80 |

[10]Cetearyl alcohol - Crodacol CS-50, Croda Inc
[11]Trideceth 2 carboxamide MEA - Aminol A 15, Kao Chemicals GmbH
[12]Ceteareth-30 - Eumulgin ™ B 3, Cognis GmbH
[13]Pentasodium pentetate - Versenex 80, Dow Chemicals
[19]Acrylates/C10-30 alkyl acrylate crosspolymer, Carbopol ™ Ultrez 20, Noveon Inc.
[20]Magnesium Stearate - Radiastar ™ 1100, Oleon NV
[21]Diethylhexyl sodium sulfosuccinate, Geropon SS-0-75, Rhodia Inc.
[22]VP/VA copolymer - Luviskol ™ VA73E BASF Corporation
[23]Polydecene - Puresyn ™ 1000 ExxonMobil Chemical Company The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments or the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for treating the hair comprising: a device and a composition;
    wherein said device comprises a first portion movably joined by a connection to a second portion; wherein said composition comprises a percentage X of hydrogen peroxide by weight of said composition and a percentage Y of an alkalizer by weight of said composition; wherein said composition comprises a minimum of 2% of hydrogen peroxide by weight of said composition; and wherein said weight percentages of said hydrogen peroxide and said alkalizer in said composition are as defined by equation (I); wherein equation (I) is $$X+1.5Y \geq 15\% \quad \text{(I)};$$

wherein said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof;
    wherein said composition further comprises a persulfate salt; and
    wherein said persulfate salt comprises a mixture of ammonium persulfate and potassium persulfate.

2. The system according to claim 1, wherein said first portion of said device is either a plate or a well and wherein said second portion of said device is either a plate or a well.

3. The system according to claim 1, wherein said connection is a hinge.

4. The system according to claim 1, wherein said first portion is a well, which comprises a base, a wall and a rim and wherein said base, said wall and said rim define an opening and an internal volume of said well; wherein said second portion is a plate, which comprises a perimeter, an internal and an external surface; wherein said internal surface of said plate may be brought into a juxtaposed relationship to said opening of said well.

5. The system according to claim 4, wherein at least a member (40) projects from said internal surface of said plate.

6. The system according to claim 4, wherein at least a first fin projects from said internal surface of said plate.

7. The system according to claim 1, wherein the ratio within said mixture between said ammonium persulfate and said potassium persulfate is from about 5:95 to about 50:50.

8. The system according to claim 1, wherein said alkalizer is a mixture of sodium silicate and a salt of hydrogen carbonate.

9. The system according to claim 8, wherein said mixture comprises a ratio of said sodium silicate and of said salt of hydrogen carbonate of from about 90:10 to about 60:40.

10. The system according to claim 1, wherein said composition further comprises a component selected from the group consisting of one or more thickeners, one or more colour indicators and combinations thereof.

11. A kit comprising one or more device, and at least a first and a second individually packaged component to form said composition according to claim 1;
    wherein said device comprises a first portion movably joined to a second portion;
    wherein said first individually packaged component comprises hydrogen peroxide and wherein said second individually packaged component comprises an alkalizer;
    and wherein said alkalizer is an inorganic salt selected from the group consisting of sodium silicate, sodium metasilicate, potassium hydrogen carbonate, ammonium carbonate, ammonium hydrogen carbonate and sodium hydrogen carbonate and mixtures thereof.

12. The kit according to claim 11, further comprising instructions for using said device, to prepare and/or to apply said composition.

\* \* \* \* \*